Figure 1:
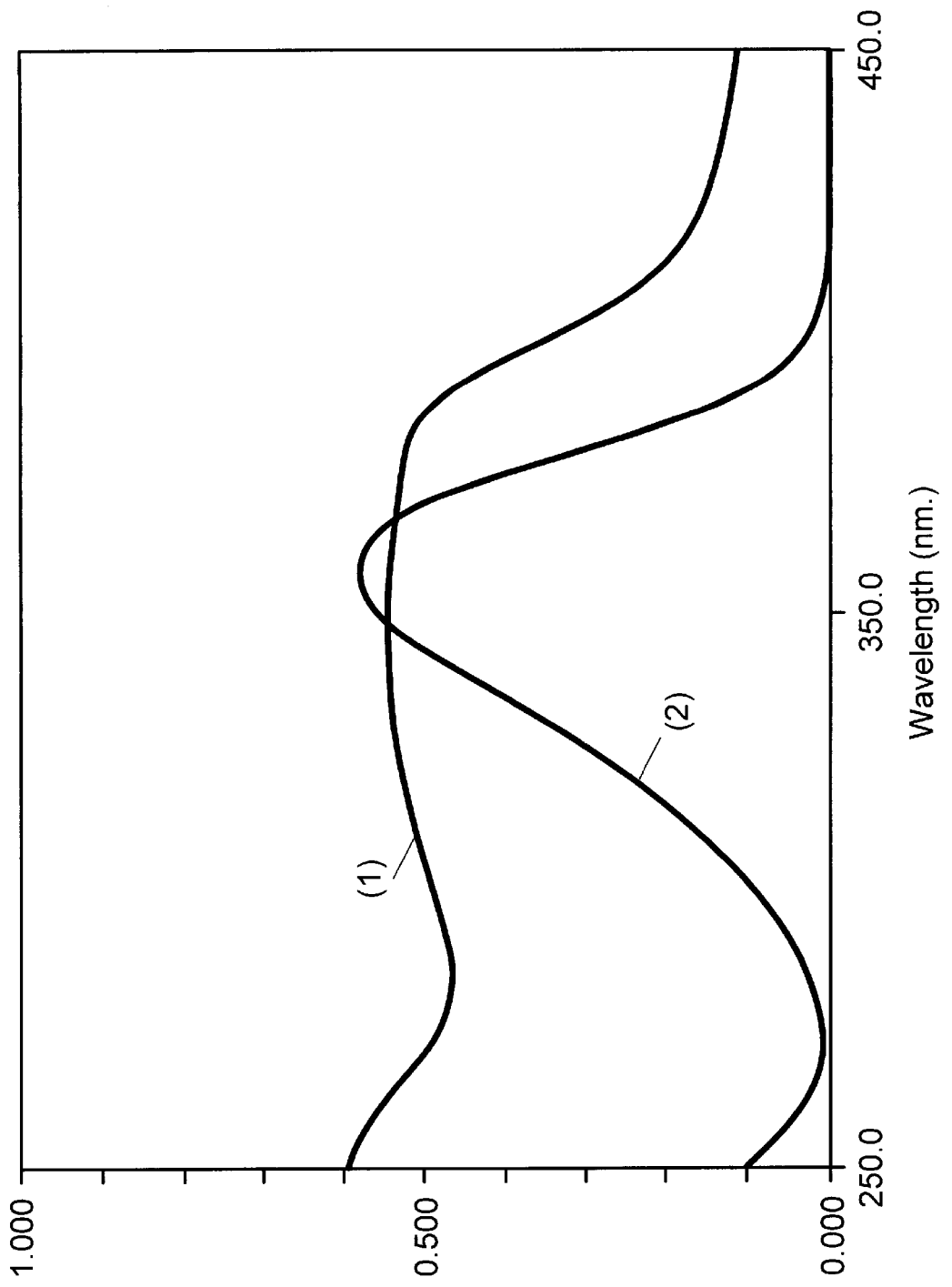

United States Patent [19]
Richard et al.

[11] Patent Number: 5,928,630
[45] Date of Patent: Jul. 27, 1999

[54] BENZALMALONATE/ PHENYLCYANOACRYLATE-SUBSTITUTED S-TRIAZINE COMPOUNDS AND PHOTOPROTECTIVE/COSMETIC COMPOSITIONS COMPRISED THEREOF

[75] Inventors: Hervé Richard, Villepinte; Madeleine Leduc, Paris; Alain LaGrange, Coupvray; Hervé Plessix, Bourg la Reine, all of France

[73] Assignee: Societe L' Oreal S.A., Paris, France

[21] Appl. No.: 09/148,497

[22] Filed: Sep. 4, 1998

Related U.S. Application Data

[62] Division of application No. 08/798,136, Feb. 12, 1997.

[30] Foreign Application Priority Data

Feb. 12, 1996 [FR] France .................... 96-01692

[51] Int. Cl.$^6$ .............. A61K 7/42; A61K 7/00; A61D 31/53
[52] U.S. Cl. .............. 424/59; 424/60; 424/400; 424/401; 514/241; 544/197; 544/211
[58] Field of Search ................ 424/59, 60, 400, 424/401; 514/241; 544/197, 211

[56] References Cited

U.S. PATENT DOCUMENTS 5,849,909  12/1998  Richard et al. .............. 544/197

FOREIGN PATENT DOCUMENTS 0507692  10/1992  European Pat. Off. .
0570691  10/1992  European Pat. Off. .
4105923   8/1992  Germany .

*Primary Examiner*—Shelley A. Dodson
*Attorney, Agent, or Firm*—Burns, Doane, Swecker & Mathis, L.L.P.

[57] ABSTRACT

Photoprotective/cosmetic compositions well suited for enhanced photoprotection of human skin and/or hair, as well as of a wide variety of other photosensitive materials and substrates, e.g., inorganic or organic glasses, plastics or the like, against the deleterious effects of UV-A and UV-B irradiation, particularly solar radiation, comprise a photoprotecting effective amount of a novel insoluble benzalmalonate/phenylcyanoacrylate-substituted s-triazine compound having the structural formula (I):

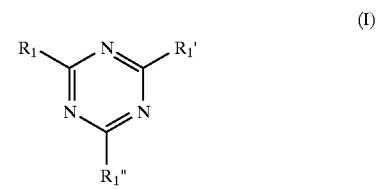

in which $R_1$, $R_1'$ and $R_1''$, which may be identical or different, are each a monovalent radical having one of the formulae (A) or (B) below:

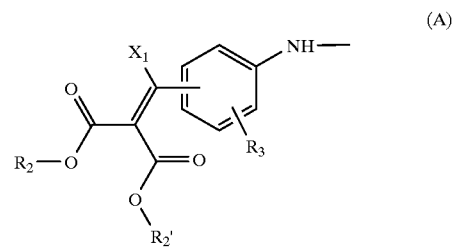

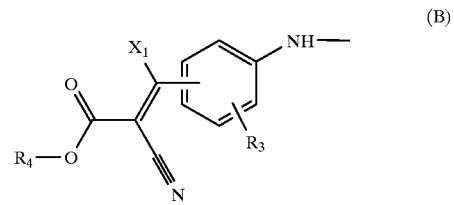

17 Claims, 2 Drawing Sheets

BENZALMALONATE/PHENYLCYANOACRYLATE-SUBSTITUTED S-TRIAZINE COMPOUNDS AND PHOTOPROTECTIVE/COSMETIC COMPOSITIONS COMPRISED THEREOF

This application is a divisional, of application Ser. No. 08/798.136, filed Feb. 12, 1997.

BACKGROUND OF THE INVENTION

1. Technical Field of the Invention

The present invention relates to novel insoluble s-triazine compounds bearing benzalmalonate and/or phenylcyanoacrylate substituents, to a process for the preparation thereof and to the use of same in particulate form as UV screening agents, in particular in the cosmetics field.

The present invention also relates to the use of such novel compounds for photoprotecting the skin and/or the hair against ultraviolet radiation, or for photoprotecting any other UV sensitive material or substrate (inorganic or organic glasses, plastics or the like).

2. Description of the Prior Art

It is known to this art that light radiation of wavelengths of from 280 nm to 400 nm promotes tanning of the human epidermis, and that light rays of wavelengths from 280 nm to 320 nm, i.e., UV-B irradiation, cause skin burns and erythema which may be harmful to the development of a natural tan; such UV-B radiation should thus be screened from the skin.

It is also known to this art that UV-A radiation, of wavelengths of from 320 nm to 400 nm, which causes tanning of the skin, is prone to induce an adverse change therein, especially in the case of sensitive skin or of skin which is continually exposed to solar radiation. UV-A irradiation causes, in particular, a loss in the elasticity of the skin and the appearance of wrinkles, promoting premature skin aging. Such irradiation promotes triggering of the erythemal reaction or amplifies this reaction in certain individuals and may even be the source of phototoxic or photoallergic reactions. Thus, it is desirable to also screen out UV-A radiation.

A wide variety of compounds useful as sunscreens, essentially in the form of soluble organic screening agents or insoluble inorganic compounds, are known to this art. These screening agents must be able to absorb or block the harmful rays of the sun, while at the same time remaining harmless to the user.

In this respect, and to limit the possible risks of allergy on the skin generated by organic screening agents on account of their solubility, inorganic pigments such as zinc oxide or titanium dioxide are increasingly used to screen out UV irradiation. However, these inorganic pigments present the drawback of being sensitive to solar radiation (phenomenon known as "photobluing"). Moreover, for equivalent amounts, these inorganic pigments are less effective in UV protection than the aforesaid organic screening agents.

SUMMARY OF THE INVENTION

It has now surprisingly been determined that certain novel non-inorganic insoluble UV screening agents are suitable for absorbing both in the UV-A range and in the UV-B range, and which have the advantage of simultaneously combining properties of diffusion, since they are solid organic pigments, and of absorption.

Briefly, the present invention features novel compounds having the following formula (I):

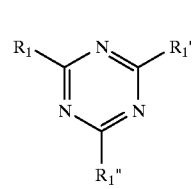

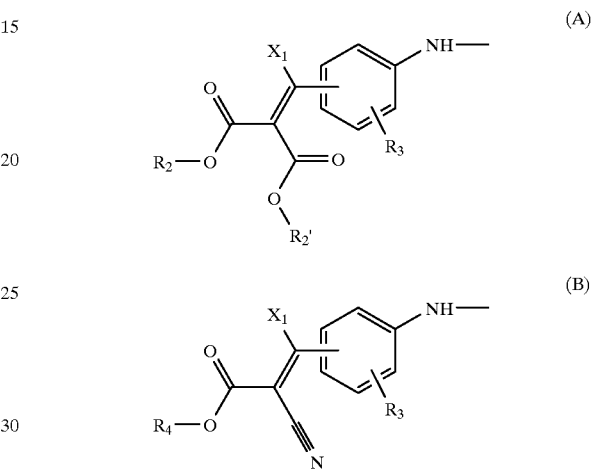

in which $R_1$, $R_1'$ and $R_1''$, which may be identical or different, are each a monovalent radical having one of the formulae (A) or (B) below:

wherein $R_2$ and $R_2'$, which may be identical or different, are each a linear or branched $C_1-C_3$ alkyl radical; $R_3$ is a hydrogen atom, a linear or branched $C_1-C_4$ alkyl radical or a $C_1-C_4$ alkoxy radical; $R_4$ is a linear or branched $C_1-C_{12}$ alkyl radical; and $X_1$ is a hydrogen atom or a phenyl radical optionally substituted with a halogen atom or with a $C_1-C_4$ alkyl radical or $C_1-C_4$ alkoxy radical.

DETAILED DESCRIPTION OF BEST MODE AND SPECIFIC/PREFERRED EMBODIMENTS OF THE INVENTION

More particularly according to the present invention, the preferred compounds of formula (I) are those in which the radicals $R_1$, $R_1'$ and $R_1''$ are identical.

Other preferred compounds of the present invention are those corresponding to formula (I) in which the radicals $R_1$, $R_1'$ and $R_1''$ are identical and each is a radical of formula (A).

In another preferred embodiment of the invention, the compounds of formula (I) are those in which the radicals $R_1$, $R_1'$ and $R_1''$ are identical and each is a radical of formula (B).

It should be appreciated that triazine derivatives bearing benzalmalonate and/or benzylidenecamphor and/or cinnamate function(s) are described in EP-A-0,507,691, EP-A-0,507,692 and DE-A-41,05,923. However, these compounds of the prior art are soluble and, moreover, absorb only in the UV-A range.

In contradistinction thereto, and as indicated above, the derivatives of the invention are insoluble compounds capable of simultaneously absorbing in the UV-A range and in the UV-B range. The benzalmalonate and phenylcyanoacrylate substituents are screening units which generally absorb UV-A radiation. The novel insoluble compounds in accordance with the present invention, substituted with benzalmalonate and/or phenylcyanoacrylate groups, present the unexpected and surprising advantage of absorbing both in the UV-A range and in the UV-B range.

Moreover, other than their screening and dispersing properties, these novel s-triazine compounds have good chemical and photochemical stability. On account of their insolubility, they present few risks of penetration into the epidermis. These compounds are therefore all suitable for the formulation of compositions intended for protecting the skin and the hair against solar irradiation.

For the purposes of this invention, by the expression "insoluble" or "substantially insoluble" compound is intended a compound whose solubility in water is less than 0.1% by weight, whose solubility in liquid petrolatum is less than 1% by weight and, lastly, whose solubility in a mixture of triglyceride esters such as "Miglyol 812" marketed by Dynamit Nobel is less than 2%, also by weight.

The present invention also features a process for the preparation of the compounds of formula (I).

Thus, the compounds of formula (I) may be prepared according to the following reaction scheme:

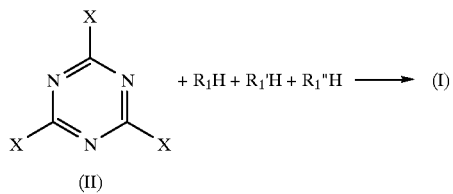

wherein $R_1$, $R_1'$ and $R_1''$ are as defined above and X is a halogen atom, in particular chlorine or bromine.

In the event that $R_1$, $R_1'$ and $R_1''$ are different, the compounds $R_1H$, $R_1'H$ and $R_1''H$ may be introduced into the reaction mixture separately and successively. Thus, in a first step, $R_1'H$ is introduced when $R_1H$ has completely reacted with the compound of formula (II). In a second step, $R_1''H$ is introduced when $R_1'H$ has completely reacted with the compound of formula (II) monosubstituted with $R_1$.

The compounds $R_1H$ (or $R_1'H$ and $R_1''H$, respectively), wherein $R_1$ (or $R_1'$ and $R_1''H$, respectively) is a radical of formula (A), may be prepared according to known techniques described, in particular, in GB-1,064,116.

The compounds $R_1H$ (or $R_1'H$ and $R_1''H$, respectively), wherein $R_1$ (or $R_1'$ and $R_1''$, respectively) is a radical of formula (B), may be prepared according to known techniques described, in particular, in *J. Soc. Dvers Colour*, 93, pp. 126–133 (1977).

The above reactions may optionally be carried out in the presence of a solvent (toluene, xylene or acetone/water).

Among the above compounds $R_1H$ which are particularly exemplary are the following:

dimethyl 4-aminobenzalmalonate;

diethyl 4-aminobenzalmalonate;

di-n-propyl 4-aminobenzalmalonate;

diisopropyl 4-aminobenzalmalonate;

ethyl α-cyano-4-aminocinnamate;

isopropyl α-cyano-4-aminocinnamate; and 2-ethylhexyl α-cyano-4-aminocinnamate.

Among the compounds of formula (I) which are particularly exemplary are the following:

2,4,6-tris(diethyl 4'-aminobenzalmalonate)-s-triazine;

2,4,6-tris(diisopropyl 4'-aminobenzalmalonate)-s-triazine;

2,4,6-tris(dimethyl 4'-aminobenzalmalonate)-s-triazine; and 2,4,6-tris(ethyl α-cyano-4-aminocinnamate)-s-triazine.

These novel insoluble or substantially insoluble s-triazine compounds may be provided in a suitable particulate form by any ad hoc means such as, in particular, dry-grinding or grinding in a solvent medium, screening, atomization, micronization or spraying. They may then be used as pigments for protecting human skin and the hair against solar radiation. They may also be used as photoprotective agents in the plastics industry, in the glass industry (packaging, optical glasses, in particular for making spectacles) and the like.

The present invention also features compositions suited to protect a material or substrate which is sensitive to ultraviolet radiation, in particular to solar radiation, comprising an effective amount of at least one compound of formula (I).

More particularly, when the sensitive material to be protected is the skin and/or the hair, this composition is in the form of a cosmetic composition comprising, in a cosmetically acceptable medium (e.g., vehicle, diluent or carrier), an effective photoprotective amount of at least one compound of formula (I).

Preferably, the compounds according to the invention are formulated into cosmetic compositions in particulate form, the average size of the particles being less than 20 μm.

The compound or compounds of formula (I) are advantageously present in the subject cosmetic compositions of the invention in proportions ranging from 0.1% to 20% by weight, relative to the total weight of the composition, preferably in an amount ranging from 0.1% to 15% by weight thereof.

The cosmetic compositions of the invention may be used as compositions for protecting the human epidermis or hair against ultraviolet irradiation, or as sunscreen compositions.

The compositions according to the invention may of course contain one or more complementary hydrophilic or lipophilic sunscreens which are active in the UV-A and/or UV-B range (absorbers). These complementary screening agents may be selected, in particular, from among the cinnamic derivatives, salicylic derivatives, camphor derivatives, triazine derivatives other than the compounds of the present invention, benzophenone derivatives, dibenzoylmethane derivatives, β,β-diphenylacrylate derivatives, p-aminobenzoic acid derivatives, and the sunscreen polymers and sunscreen silicones described in WO-93/04665. Other examples of organic screening agents are set forth in EP-A-0,487,404.

The compositions according to the invention may also contain agents for the artificial tanning and/or browning of the skin (self-tanning agents) such as, for example, dihydroxyacetone (DHA).

The compositions of this invention may also contain pigments or, alternatively, nanopigments (average size of the primary particles: generally ranging from 5 nm to 100 nm, preferably from 10 nm to 50 nm) of coated or uncoated metal oxides such as, for example, nanopigments of titanium dioxide (amorphous or crystallized in rutile and/or anatase state), of iron oxide, of zinc oxide, of zirconium oxide or of cerium oxide, which are all UV photoprotective agents that are per se well known to this art. Standard coating agents include alumina and/or aluminum stearate. Such coated or uncoated metal oxide nanopigments are described, in particular, in EP-A-0,518,772 and EP-A-0,518,773.

The compositions of the invention may also comprise conventional cosmetic additives and adjuvants selected, in particular, from among fatty substances, organic solvents, ionic or nonionic thickeners, softeners, antioxidants, opacifying agents, stabilizers, emollients, silicones, α-hydroxy acids, anti-foaming agents, moisturizers, vitamins, fragrances, preservatives, surfactants, fillers, sequestering agents, polymers, propellants, basifying or acidifying agents, dyes, pigments, colorants, or any other ingredient typically formulated into cosmetics, in particular for the production of sunscreen compositions in the form of emulsions.

The fatty substances may be an oil or a wax or mixtures thereof, and may also comprise fatty acids, fatty alcohols and fatty acid esters. The oils may be selected from among animal, plant, mineral or synthetic oils and, in particular, from liquid petrolatum, liquid paraffin, volatile or non-volatile silicone oils, isoparaffins, poly-α-olefins, and fluoro and perfluoro oils. Similarly, the waxes may be selected from among animal, fossil, plant, mineral or synthetic waxes that are per se well known to this art.

Exemplary organic solvents include the lower alcohols and polyols.

The thickeners may be selected, in particular, from among crosslinked polyacrylic acids, guar gums and cellulose gums that are modified or unmodified, such as hydroxypropyl guar gum, methylhydroxyethylcellulose, hydroxypropylmethylcellulose or hydroxyethylcellulose.

Naturally, one skilled in this art will take care to select the optional complementary compound or compounds indicated above and/or the amounts thereof such that the advantageous properties intrinsically associated with the compounds in accordance with the invention are not, or are substantially not, adversely affected by the addition or additions envisaged.

When the compositions according to the invention are used for protecting the human epidermis against UV irradiation, or as sunscreen compositions, they may be formulated as a suspension or dispersion in solvents or fatty substances, in the form of a nonionic vesicle dispersion or, alternatively, in the form of an emulsion, preferably of oil-in-water type, such as a cream or a milk, or in the form of an ointment, a gel, a cream gel, a lotion, a solid stick, a pencil, an aerosol foam or a spray.

When the compositions of this invention are used for protecting the hair, they may be formulated as a shampoo, a lotion, a gel, an emulsion, a nonionic vesicle dispersion or a hair lacquer and may constitute, for example, a rinse-out composition, to be applied before or after shampooing, before or after dyeing or bleaching, before, during or after permanent-waving or straightening of the hair, a styling or treating lotion or gel, a blow-drying or hair-setting lotion or gel, or a composition for the permanent-waving, straightening, dyeing or bleaching of the hair.

The compositions of the invention may be formulated according to techniques which are well known to this art, in particular those for the preparation of emulsions of oil-in-water or water-in-oil type.

When the sensitive material to be protected is an organic and/or inorganic glass or a plastic, the compositions according to the invention may be in the form of a varnish which is applied to said sensitive material such as to protect it against ultraviolet radiation.

The present invention also features the formulation of at least one compound of formula (I) into compositions for the photoprotection of materials and substrates which are sensitive to UV radiation, in particular solar radiation.

In particular, this invention features the formulation of at least one compound of formula (I) into cosmetic compositions for photoprotecting the skin and/or the hair against ultraviolet radiation, in particular solar radiation.

Too, the present invention features the formulation of at least one compound of formula (I) into varnishes for photoprotecting organic and/or inorganic glasses or plastics against ultraviolet radiation, in particular solar radiation.

The compounds of the invention may also be incorporated directly into plastics, or into other materials and substrates which are sensitive to ultraviolet radiation, to protect same against the deleterious effects of said radiation.

The present invention thus also features a technique for protecting a material or substrate which is sensitive to ultraviolet radiation and/or solar radiation against said radiation, entailing applying to, or incorporating into, said sensitive material or substrate an effective amount of at least one compound of formula (I) or a composition containing at least one compound of formula (I).

In particular, the regimen according to the invention entails applying an effective amount of a cosmetic composition as described above to human skin and/or hair.

In another embodiment of the invention, the subject technique entails incorporating an effective amount of at least one compound of formula (I) or a composition containing at least one compound of formula (I) into a polymer or plastic to protect said polymer or plastic against ultraviolet radiation, in particular against solar radiation.

Thus, this invention features plastic or polymer compositions photoprotected by such technique.

In another embodiment of the invention, the subject technique entails applying an effective amount of said at least one compound or said composition to a face surface of an inorganic or organic glass.

Accordingly, also featured are glass compositions thus photoprotected.

In order to further illustrate the present invention and the advantages thereof, the following specific examples are given, it being understood that same are intended only as illustrative and in nowise limitative.

EXAMPLE 1

Preparation of 2,4,6-tris(diethvl 4'-aminobenzalmalonate)-s-triazine:

Cyanuric chloride (0.92 g, $5 \times 10^{-3}$ mol) and diethyl 4-aminobenzalmalonate (3.95 g, $15 \times 10^{-3}$ mol) were heated at reflux for 10 hours under nitrogen in xylene (50 ml). The mixture was cooled and the precipitate obtained was filtered off and dried (4.3 g, yield=60%). After recrystallization from absolute ethanol, a product was obtained having the following characteristics:

(a) insoluble pale yellow powder (b) m.p.: 130–140° C.

(c) UV (95% ethanol) $\lambda_{max}$=355 nm, $\epsilon_{max}$=99,400
Elemental analysis for $C_{45}H_{48}N_6O_{16}$

| theory: | C: 62.49 | H: 5.59 | N: 9.72 | O: 22.20 |
|---|---|---|---|---|
| found: | C: 62.48 | H: 5.65 | N: 9.60 | O: 22.15 |

EXAMPLE 2

Preparation of 2,4,6-tris(diisoproryl 4'-aminobenzalmalonate)-s-triazine:

Cyanuric chloride (2.12 g, 0.0115 mol) and diisopropyl 4-aminobenzalmalonate (11 g, 0.0377 mol) were heated at reflux for 6 hours under nitrogen in xylene (60 ml). The mixture was concentrated under vacuum and recrystallized from ethanol to obtain a product (7.3 g, yield=67%) having the following characteristics:

(a) insoluble pale yellow powder
(b) m.p.: 181° C.
(c) UV (95% ethanol) $\lambda_{max}$=355 nm, $\epsilon_{max}$=111,000
Elemental analysis for $C_{51}H_{60}N_6O_{12}$

| theory: | C: 64.54 | H: 6.37 | N: 8.85 | O: 20.23 |
|---------|----------|---------|---------|----------|
| found:  | C: 64.76 | H: 6.41 | N: 8.80 | O: 20.09 |

The UV spectrum of solid 2,4,6-tris(diisopropyl 4'-aminobenzalmalonate)-s-triazine (curve (1)) and the UV spectrum in ethanol of the soluble compound which is chemically the most similar, namely, 2,4,6-tris(diisobutyl 4'-aminobenzalmalonate)-s-triazine (curve (2)), the synthesis of which is described in EP-A-0,507,691, assigned to the assignee hereof, are shown in FIG. 1 on the same scale (wavelength on the x-axis, absorbance on the y-axis).

The spectra were obtained using a Shimadzu UV 2101 PC spectrophotometer.

The 2,4,6-tris(diisobutyl 4'-aminobenzalmalonate)-s-triazine was solubilized to a concentration of 5 mg/l in 95% ethanol.

The crude 2,4,6-tris(diisopropyl 4'-aminobenzalmalonate)-s-triazine was screened through a 50 μm screen of stainless steel-stainless steel weave mounting. It was then dispersed in white petrolatum marketed under the trademark "Codex 236" by Sarega at the melting point of the petrolatum and in a proportion of 5 g of screened 2,4,6-tris(diisopropyl 4'-aminobenzalmalonate)-s-triazine per 100 g of petrolatum. This mixture was then treated with ultrasound to ensure homogeneous dispersion. A film 60 μm in thickness was analyzed.

FIG. 1 clearly indicates that the insoluble compound according to the present invention, namely, 2,4,6-tris (diisopropyl 4'-aminobenzalmalonate)-s-triazine, absorbs over the entire UV radiation range (280–400 nm).

EXAMPLE 3

Figure 2:
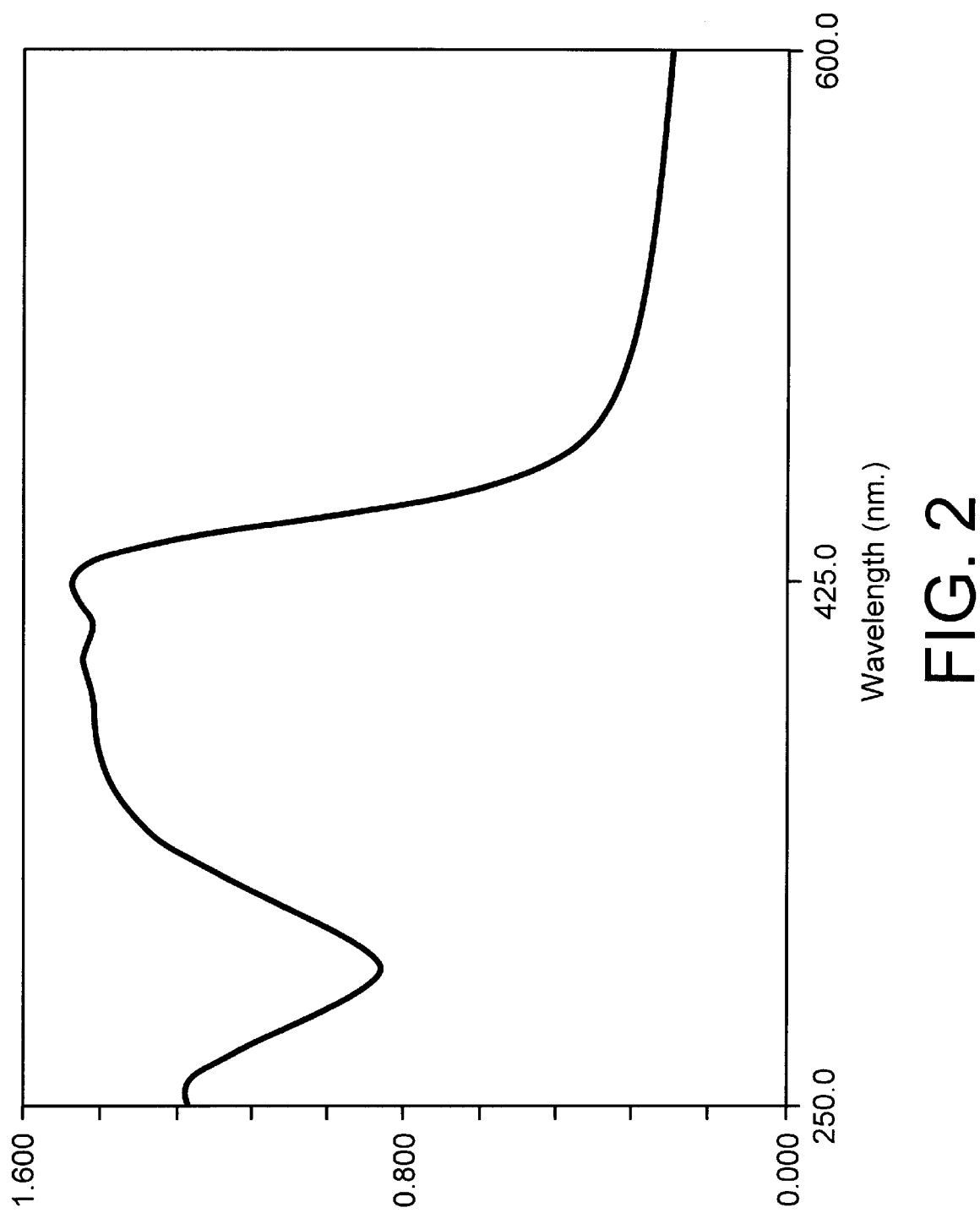

Preparation of 2,4,6-tris(ethyl α-cyano-4-aminocinnamate) -s-triazine:

Cyanuric chloride (1.1 g, 6 mmol) and ethyl α-cyano-4-aminocinnamate (4.32 g, 0.02 mol) were heated at reflux for 12 hours under nitrogen in xylene (100 ml). The mixture was filtered and the yellow powder was washed with xylene and then with ethanol to obtain a product (3 g, yield=69%) having the following characteristics:

(a) insoluble golden-yellow powder
(b) m.p.: >300° C.
(c) UV (DMSO) $\lambda_{max}$=390 nm. Solid UV spectrum (5 g of 2,4,6-tris(ethyl α-cyano-4-aminocinnamate)-s-triazine per 100 g of "Codex 236" petrolatum): cf. FIG. 2.
(d) absorption: continuous from 320 to 350 nm.

EXAMPLE 4

This example is of a cosmetic composition in the form of an emulsion of oil-in-water type (the amounts are expressed as a % by weight relative to the total weight of the composition):

(1) mixture of cetylstearyl alcohol and of cetylstearyl alcohol oxyethylenated with 33 mol of ethylene oxide, marketed under the trademark

| (1) | mixture of cetylstearyl alcohol and of cetylstearyl alcohol oxyethylenated with 33 mol of ethylene oxide, marketed under the trademark "Sinnowax AO" by Henkel | 7% |
|-----|---|-----|
| (2) | non-self-emulsifiable mixture of glyceryl mono- and distearate | 2% |
| (3) | cetyl alcohol | 1.5% |
| (4) | silicone oil | 1.5% |
| (5) | diisopropyl adipate | 15% |
| (6) | 2,4,6-tris(diethyl 4'-aminobenzalmalonate)-s-triazine (screening agent) | 5% |
| (7) | glycerol | 20% |
| (8) | fragrance, preservatives | qs |
| (9) | water | qs 100% |

This composition was formulated in the following manner: after preparing the emulsion, the screening agent was dispersed therein at about 40° C. The cream obtained was then homogenized in a tri-cylinder.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective/cosmetic composition of matter, comprising an effective UV-A and UV-B photoprotecting amount of at least one benzlmalonate/phenylcyanoacrylate-substituted s-triazie compound having the structural formula (I):

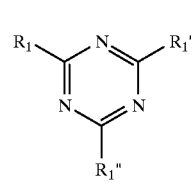

in which $R_1$, $R_1'$ and $R_1''$, which may be identical or different, are each a monovalent radical having one of the formulae (A) or (B) below:

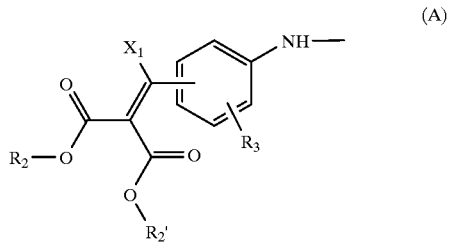

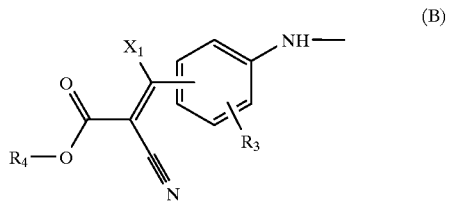

wherein $R_2$ and $R_2'$, which may be identical or different, are each a linear or branched $C_1$–$C_3$ alkyl radical; $R_3$ is a hydrogen atom, a linear or branched $C_1$–$C_4$ alkyl radical or a $C_1$–$C_4$ alkoxy radical, $R_4$ is a linear or branched $C_1$–$C_{12}$ alkyl radical; and $X_1$ is a hydrogen atom or a phenyl radical optionally substituted with a halogen atom or with a $C_1$–$C_4$, alkyl radical or $C_1$–$C_4$ alkoxy radical in an acceptable vehicle, diluent or carrier therefor.

2. A normally photosensitive substrate comprising an effective UV-A and UV-B photoprotecting amount of at least one benzalmalonate/phenylcyanoacrylate-substituted s-triazine compound as defined by claim 1.

3. The photosensitive substrate as defined by claim 2, comprising an inorganic or organic glass, a polymer or a plastic.

4. The photosensitive substrate as defined by claim 3, said at least one benzalmalonate/phenylcyanoacrylate-substituted s-triazine compound being incorporated therein.

5. The photosensitive substrate as defined by claim 3, said at least one benzalmalonate/phenylcyanoacrylate-substituted s-triazine compound being coated thereon.

6. A topically applicable photoprotective/cosrnetic composition of matter adopted for the photoprotection of human skin and/or hair, comprising an effective UV-A and UV-B photoprotecting amount of at least one benzalmalonate/phenylcyanoacrylate-substituted s-triazine compound as defined by claim 1, in a cosmetically acceptable topical vehicle, carrier or diluent therefor.

7. The photoprotective/cosmetic composition as defined by claim 6, comprising from 0.1% to 15% by weight of said at least one benzalmalonate/phenylcyanoacrylate-substituted s-triazine compound.

8. The photoprotective/cosmetic composition as defined by claim 6, further comprising at least one complementary hydrophilic or lipophilic sunscreen.

9. The photoprotective/cosmetic composition as defined by claim 6, further comprising at least one artificial tanning/browning agent.

10. The photoprotective/cosmetic composition as defined by claim 6, further comprising at least one metal oxide pigment or nanopigment.

11. The photoprotective/cosmetic composition as defined by claim 6, further comprising at least one conventional cosmetic additive and/or adjuvant.

12. The photoprotective/cosmetic composition as defined by claim 11, said at least one additive/adjuvant comprising a fatty substance, an organic solvent, an ionic or nonionic thickener, a softener, an antioxidant, an opacifying agent, a stabilizer, an emollient, a silicone, an a-hydroxy acid, an anti-foaming agent, a moisturizer, a vitamin, a fragrance, a preservative, a surfactant, a filler, a sequestering agent, a polymer, a propellant, a basifying or acidifying agent, a dye, a pigment, or a colorant.

13. The photoprotective/cosmetic composition as defined by claim 6, comprising an oil-in-water or water-in-oil emulsion.

14. The photoprotective/cosmetic composition as defined by claim 6, comprising a suspension or dispersion, a non-ionic vesicle dispersion, a cream, a milk, an ointment, a gel, a cream gel, a lotion, a solid stick, a pencil, an aerosol foam or a spray.

15. The photoprotective/cosmetic composition as defined by claim 6, comprising a shampoo, a hair lacquer, a rinse-out composition, a styling or treating lotion or gel, a blow-drying or hair-setting lotion or gel, or a composition for the permanent-waving, straightening, dyeing or bleaching of the hair.

16. A method for protecting human skin and/or hair against the deleterious effects of ultraviolet irradiation, comprising topically applying thereto an effective amount of the photoprotective/cosmetic composition as defined by claim 6.

17. A method for protecting human skin and/or hair against the deleterious effects of solar radiation, comprising topically applying thereto an effective amount of the photoprotective/cosmetic composition as defined by claim 6.

* * * * *